(12) United States Patent
Cheng et al.

(10) Patent No.: US 9,605,023 B2
(45) Date of Patent: Mar. 28, 2017

(54) APPLICATION OF SP PEPTIDE OR DERIVATIVE THEREOF IN PREPARING MEDICINES FOR PREVENTING OR TREATING ASTHMA

(71) Applicants: Yun Cheng, Beijing (CN); Ruihe Yu, Beijing (CN)

(72) Inventors: Yun Cheng, Beijing (CN); Ruihe Yu, Beijing (CN); Hong Li, Beijing (CN); Wanzhou Zhao, Beijing (CN)

(73) Assignees: Yun Cheng, Beijing (CN); Ruihe Yu, Beijing (CN)

( * ) Notice: Subject to any disclaimer, the term of this patent is extended or adjusted under 35 U.S.C. 154(b) by 22 days.

(21) Appl. No.: 14/742,656

(22) Filed: Jun. 17, 2015

(65) Prior Publication Data

US 2015/0284430 A1 Oct. 8, 2015

Related U.S. Application Data

(63) Continuation of application No. PCT/CN2012/086830, filed on Dec. 18, 2012.

(51) Int. Cl.
*C07K 7/06* (2006.01)
*A61K 38/08* (2006.01)
*A61K 38/00* (2006.01)

(52) U.S. Cl.
CPC ............... *C07K 7/06* (2013.01); *A61K 38/08* (2013.01); *A61K 38/00* (2013.01)

(58) Field of Classification Search
None
See application file for complete search history.

(56) References Cited

U.S. PATENT DOCUMENTS

2008/0227723 A1* 9/2008 Cheng .................... A61K 38/08
514/1.4

FOREIGN PATENT DOCUMENTS

| CN | 1438238 A | 8/2003 |
|---|---|---|
| CN | 1194986 C | 3/2005 |
| CN | 1216075 C | 8/2005 |
| CN | PCT/CN2006/6001176 | 6/2006 |
| CN | 101559217 A | 10/2009 |
| CN | 101822816 A | 9/2010 |
| CN | 101336110 B | 6/2011 |
| CN | 102178926 A | 9/2011 |
| CN | 102229645 A | 11/2011 |

OTHER PUBLICATIONS

Chung, F. Mediators of Inflammation. 10, 51-59 (2001).*
The Chinese First Examination Report of corresponding China patent application No. 201280077242.X, dated Mar. 7, 2016.
Huang, Ji-Han et al., "Dose conversion among different animals and healthy volunteers in pharmacological study" Chinese Journal of clinical Pharmacology and Therapeutics, Issue 9, (2004), p. 1069-1072.
International Search Report of corresponding International PCT Application No. PCT/CN2012/086830, dated Sep. 26, 2013.

\* cited by examiner

*Primary Examiner* — Amber D Steele
*Assistant Examiner* — Schuyler Milton
(74) *Attorney, Agent, or Firm* — J.C. Patents (57) ABSTRACT

The present invention provides an application of an SP peptide or a derivative thereof in preparing medicines for preventing or treating asthma. The peptide or the derivative thereof is the SP peptide shown in Formula I or a pharmaceutically acceptable salt or ester thereof. The present invention also provides a method for treating asthma, the method comprises: administering to a patient with medicine containing the peptide or the derivative thereof with an effective therapeutic dosage. It proves through researches of the present invention that, the peptide or the derivative thereof can effectively alleviate pathological symptoms of asthma, especially pathological symptoms of allergic asthma. In the formula (I), Xaa1 is deletion, Ala, Gly, Val, Leu or Ile; Xaa2 is Thr or Ser; Xaa3 is Tyr, Phe or Trp; and Xaa4 is deletion, Ala, Gly, Val, Leu, Ile or Pro.

Xaa1-Gln-Xaa2-Xaa3-Thr-Ser-Gly-Xaa4 (Formula I)

19 Claims, 8 Drawing Sheets

APPLICATION OF SP PEPTIDE OR DERIVATIVE THEREOF IN PREPARING MEDICINES FOR PREVENTING OR TREATING ASTHMA

CROSS-REFERENCE TO RELATED APPLICATIONS

This application is a continuation of International Application No. PCT/CN2012/086830, filed on Dec. 18, 2012. The content of the above identified application is incorporated herein by reference in their entireties.

FIELD OF THE TECHNOLOGY

The present invention relates to the field of medicinal technology and, in particular, to an application of an SP peptide or a derivative thereof in preparing medicines for preventing or treating asthma, especially to an application of an SP peptide or a derivative thereof in preparing medicines for preventing or treating allergic asthma.

BACKGROUND

Asthma is a common respiratory system disease, the pathogenesis includes: allergic response, airway chronic inflammation, airway hyperresponsiveness, airway neuro-regulation disorder, genetic mechanism, respiratory tract virus infection, neural signal transduction mechanism, airway remodeling, as well as interactions thereof, etc. The main symptoms are paroxysmal gasping, panting, chest tightness or coughing, and the like, or original symptom rapid aggravating that usually accompanied with breathing difficulties featured by reduced expiratory gas flow, commonly induced by contacting allergen, irritant or respiratory infection. The symptoms may vary in severity, if the patient's condition is getting worse, it may appear within several hours or several days, and occasionally it may be life-threatening within several minutes. In recent years, allergic asthma induced by various allergens (such as pollens, dusts and dust mite) attracts more and more attention. Therefore, research on medicines for effectively against asthma has also become one of the primary research topics in the field.

The present inventor discloses in Chinese patents CN1194986C and CN1216075C a peptide shown in SEQ ID No.1 or a derivative thereof (abbreviated as 7P peptide or a derivative thereof, named as SP peptide or a derivative thereof in the present invention), which is an immunogenic peptide originally designed according to hepatitis C virus. In addition, it is proved that the 7P peptide or the derivative thereof has functions of inducing cytokines, such as r-IFN, IL-4 and IL-10 to an increased level and producing antibodies. r-IFN is a Th1-secreted cytokine, which is one of the primary cytokines of human immune system against virus infection, and it has a prominent meanings for the clearance of HCV (hepatitis C virus), so that the 7P peptide or the derivative thereof has functions of preventing and/or treating hepatitis C. Further, the present inventor discloses in patent application CN101822816A the application of the 7P peptide or the derivative thereof for preventing and treating pneumonia, and specifically records the 7P peptide or the derivative thereof for treating pneumonia by reducing TNF-α level. Therefore, it can be known from a report of the existing research that, the 7P peptide has functions of reducing TNF-α level of a patient with pneumonia, as well as promoting the cytokine IL-4 level of a patient with hepatitis C.

There are no reports about whether the peptide or the derivative thereof has effects on preventing asthma attacks and alleviating asthma symptoms.

SUMMARY

The present invention provides an application of the aforementioned SP peptide or the derivative thereof in preparing medicines for preventing or treating asthma, provides a new clinical method for treating or preventing diseases such as asthma, and also expands potential medicinal field of the SP peptide.

The present invention also provides a method for treating or preventing asthma by utilizing the SP peptide or the derivative thereof, and the purposes of effectively preventing an occurrence of asthma and significantly alleviating pathological symptoms of asthma can be achieved by administering to a patient with medicines containing the peptide or the derivative thereof having an effective therapeutic dosage.

The present invention also provides an application of the aforementioned SP peptide or the derivative thereof in preparing medicines for reducing IL-13 level and IL-4 level of a patient with asthma.

The present invention provides an application of an SP peptide shown in SEQ ID No.1 or a derivative thereof in preparing medicines for preventing or treating asthma:

Xaa1-Gln-Xaa2-Xaa3-Thr-Ser-Gly-Xaa4    (SEQ ID No.1)

Wherein,
Xaa1 is deletion, Ala, Gly, Val, Leu or Ile,
Xaa2 is Thr or Ser,
Xaa3 is Tyr, Phe or Trp, and
Xaa4 is deletion, Ala, Gly, Val, Leu, Ile or Pro;

The derivative includes a pharmaceutically acceptable salt or ester of the peptide.

The inventor's researches have proved that, administering an effective dosage of the SP peptide or the derivative thereof can effectively prevent or treat asthma, especially prevent or treat allergic asthma. The SP peptide or the derivative thereof shown in aforementioned SEQ ID No.1 has basic structure and composition which is equivalent to the 7P peptide or the derivative thereof obtained from the inventor's previous studies, and named as SP peptide or a derivative thereof in the present invention. According to the disclosures of prior patents, the SP peptide or the derivative thereof can be synthesized by solid phase synthesis or liquid phase synthesis methods well-known to those skilled in the art, or can be obtained by genetic engineering fusion expression and purification.

In this context, the term "pharmaceutically acceptable ester" refers to an ester suitable for use in contact with the tissues of human and animals without excessive toxicity, irritation, allergic response, etc. Generally, after an esterified modification, hydrolysis of a peptide by protease in an organism can be reduced. The pharmaceutically acceptable ester can be formed by modifying terminal amino, carboxyl or side chain groups of the peptide in the present invention. The modification to the side chain groups of an amino acid includes, but not limited to an esterification reaction between the side chain hydroxyl group of threonine and serineand carboxylic acids. The terminal group of an amino acid is preferably protected by protective groups such as acetyl, trifluoroacetyl, Fmoc (9-fluorenylmethyloxycarbonyl), Boc (tert-butoxycarbonyl), Alloc (allyloxycarbonyl), $C_{1-3}$ alkyl and $C_{6-12}$ aralkyl, and the like, known to technologists in the field of protein chemistry. The medicinal ester in relation to the SP peptide (that is, the 7P peptide in the prior patent) has been described in international application No. PCT/CN2006/001176 in details, thus the relevant contents of the disclosed prior application documents are introduced herein as reference. In the specific embodiments of the present invention, the inventor found out that the peptide in the present invention without modification is also satisfactory for the treatment or prevention of asthma under physiological condition. Therefore, it is preferable not to modify the amino of N-terminal, the carboxyl of C-terminal, as well as the side chain groups of an amino acid of a polypeptide in SEQ ID No.1, that is, the chemical groups of N-terminal is still α-amino (—$NHB_{2B}$) in the first amino acid, and the chemical groups of C-terminal is carboxyl (—COOH) of C-terminal of an amino acid.

In this context, the term "pharmaceutically acceptable salt" refers to a salt suitable for use in contact with the tissues of human and animals without excessive toxicity, irritation, allergic response, etc. The pharmaceutically acceptable salt is well-known in the field. This type of salt can be prepared in the process of final isolation and purification of the polypeptide in the present invention, or can be prepared separately by reacting the peptide with appropriate organic or inorganic acids/bases. Representative acid addition salts include, but not limited to, acetate, adipate, alginate, citrate, aspartate, benzoate, benzenesulfonate, bisulfate, butyrate, camphorate, camphosulfonate, glycerophosphate, hemisulfate, heptanoate, hexanoate, fumarate, hydrochloride, hydrobromide, hydroiodide, 2-hydroxyethane-sulfonate, lactate, maleate, methanesulfonate, nicotinate, 2-naphthalenesulfonate, oxalate, 3-phenyl propionate, propionate, succinate, tartrate, phosphate, glutamate, bicarbonate, p-toluenesulfonate and undecanoate. Preferably, acids capable of forming the pharmaceutically acceptable salt are hydrochloric acid, hydrobromic acid, sulfuric acid, phosphoric acid, oxalic acid, maleic acid, succinic acid and citric acid. The cations in the pharmaceutically acceptable base addition salts include, but not limited to, alkali metals and alkaline earth metallic ions, such as lithium, sodium, potassium, calcium and magnesium, etc, or quaternary ammonium cations (such as tetramethyl ammonium, tetraethyl ammonium, etc), and cations of ammonium, methylamine, dimethylamine, trimethylamine, triethylamine, diethylamine, ethylamine, ethanolamine, diethanolamine, piperidine, piperazine, etc. Preferable base addition salts include phosphate, tris(hydroxymethyl)aminomethane (tris) and acetate. These salts generally can increase the solubility of the polypeptide, and the salts formed basically do not change the activities of the polypeptide.

In summary, according to the technical solutions of the present invention, the medicines for preventing and/or treating asthma can directly adopt the peptide (the SP peptide), or can adopt medicinal formulation formed by a pharmaceutically acceptable salt or ester of the SP peptide.

Further, the SP peptide or the derivative thereof is a peptide shown in SEQ ID No.2 or a pharmaceutically acceptable salt or ester thereof:

Gly-Gln-Thr-Tyr-Thr-Ser-Gly                  (SEQ ID No.2)

According to a known amino acid expression manner in the art, the SP peptide shown in SEQ ID No.2 also can be abbreviated as GQTYTSG.

In embodiments of the present invention, depending upon preventing and/or treating purposes as well as administration mode, the peptide or the derivative thereof can adopt appropriate formulation forms, for example: injection formulation, lyophilized powders (for injection), sprays, oral solutions, oral suspensions, tablets, capsules, enteric-coated tablets, pills, powders, granules, slow-release formulations (formulations is controllable to slow release of the effective component of a formulation) or controlled release formulations (formulations is controllable to release of the effective component of a formulation). The formulation can include a conventional pharmaceutically acceptable carrier, and the term "pharmaceutically acceptable carrier" refers to a non-toxic solid, semi-solid or liquid state filling agent, diluent, adjuvant, encapsulating material or other auxiliary material for formulation, such as physiological saline, isotonic glucose solution, saline buffer, glycerol, ethanol and a combination of the above solutions. In embodiments of the present invention, medicines made from the peptide or the derivative thereof are administered preferably in an injection mode, that is, preferably use injection formulations or lyophilized powder ampoules, dissolved in physiological saline carrier.

Further, the injection formulation contains the peptide or the derivative thereof having an effective therapeutic dosage from 200 to 3000 μg. Furthermore, the injection formulation contains the peptide or the derivative thereof having an effective therapeutic dosage from 250 to 2500 μg.

The present invention provides a method for treating or preventing asthma, the method includes: administering to a patient with medicines containing the peptide or the derivatives thereof shown in above SEQ ID No.1 having an effective therapeutic dosage, and the derivative includes a pharmaceutically acceptable salt or ester of the peptide.

According to preferable embodiments of the present invention, the peptide or the derivative thereof as the effective component of the medicines for the treatment can be the SP peptide shown in above SEQ ID No.2 or the pharmaceutically acceptable salt or ester thereof.

The medicines containing the SP peptide or the derivative thereof (the peptide or the derivative thereof as the effective component) having an effective therapeutic dosage can effectively prevent or treat asthma, especially prevent or treat allergic asthma. Further, administering to a patient with the medicines after asthma attacks for the treating asthma; or administering to a patient with the medicines after contacting asthma allergen within 1 to 48 hours, preferably within 1 to 24 hours for preventing asthma. The patient refers to the person with asthma allergic history or suffering from asthma.

In an embodiment of the present invention, administer to a patient with medicines containing the SP peptide or the derivative thereof having an effective therapeutic dosage from 200 to 3000 μg. More preferably, administer to a patient with medicines containing the SP peptide or the derivative thereof having an effective therapeutic dosage from 250 to 2500 μg. The effective therapeutic dosage is an effective dosage administered once based on a general weight of an adult.

In an embodiment of the present invention, preferably administer medicines containing the peptide or the derivative thereof having an effective therapeutic dosage by injection method. Further, the patient is preferably administered with a dosage of unit formulation. The unit formulation is a formulation containing required effective components can satisfy one administration, and common unit formulation such as one unit (piece) of tablet, one unit (needle) of ampoule or powder ampoule, wherein a content of the effective components is a dosage needed in one administration. The dosage required in one administration to a patient can be obtained conveniently by calculating a product of patient's weight and a unit weight dosage needed in one administration to the patient. For example, during medicines preparation, an adult weight is generally considered as 50-90 kg, which can be used for calculation. The unit weight dosage of experimental animals and that of human can be calculated by an equivalent dosage conversion relationship. For example, an effective dosage of human can be derived from the dosage of the experimental animals according to the equivalent dosage conversion relationship between experimental animals and human (may refer to the guidance of Drug Administration Institutions such as FDA and SFDA) known to those skilled in the art, or may refer to a publication (Huang, J. et al., Dose Conversion among Different Animals and Healthy Volunteers in Pharmacological Study, Chinese Journal of Clinical Pharmacology and Therapeutics. 2004 September, 9(9), 1069-1072.). In the embodiments of the present invention, it may convert dosages of human and mouse based on a body surface area conversion coefficient 0.1 between human and mouse. According to the embodiments of the present invention, when the peptide or the derivative thereof in the unit formulation is administered to a mouse with a dosage of 50-300 µg/kg for mouse, a better therapeutic effect can be achieved, while the therapeutic effect can be even better when the mouse is administered with a dosage of 60-250 µg/kg for mouse, such as a dosage of 250 µg/kg or 125 µg/kg for mouse. Pharmaceutical manufacturers can obtain a quantity of effective component for a human unit formulation based on the aforementioned conversion method, which can be applied to the pharmaceutical process thereof. In the technical solutions of the present invention, according to the equivalent dosage conversion relationship and ordinary weight of human, as well as medicinal administration safety, cost and efficacy, preferably, the unit formulation contains the peptide or the derivative thereof having a dosage from 200 to 3000 µg, more preferably, the peptide or the derivative thereof having a dosage from 250 to 2500 µg.

According to the research of the present invention, the present inventor has disclosed in patent application CN101822816A that the 7P peptide or the derivative thereof (i.e., the SP peptide or the derivative thereof in the present invention) can reduce TNF-α level of a patient with pneumonia, however, allergic asthma is generally induced by cytokines such as IL-4 and IL-13, while inflammatory factors such as TNF-α aggravate asthma. It has been adequately proven by researches that, IL-13 and IL-4 have effects on inducing asthma attacks, and a high-expression of IL-13 in lung tissues may induce inflammation, mucus hypersecretion, epithelium and hypodermis fibrosis, eosinocyte cells activation/chemotactic factor production, and airway hyperresponsiveness. IL-4 expression can enhance expression of vascular cell adhesion molecules in epithelium cells, induce airway epithelium cells to produce endotoxins, and eventually aggravate airway damage by eosinocyte cells, and promote airway inflammation.

The present applicant found through researches that, the SP peptide or the derivative thereof, when used in preventing and treating asthma, can effectively alleviate pathological symptoms of asthma, especially pathological symptoms of allergic asthma. In embodiments of the present invention, the effect of the aforementioned SP peptide or the derivative thereof on allergic asthma is illustrated based on an allergic asthma mouse model induced by conventional means in the art, that is, the allergic asthma mouse model is induced by a combination of ovalbumin and adjuvant. It can be seen from the data from the following embodiments that, compared to the model group, the groups applied with the SP peptide or the derivative thereof (including SP peptide high-/medium-/low-dosage preventive administration groups and SP peptide high-/medium-/low-dosage treatment administration groups) all exhibit a significantly reduced IL-13 and IL-4 level and a significantly alleviated lung tissue lesion level. It shows the SP peptide or the derivative thereof having a significant effect on preventing or treating asthma.

Therefore, the present invention further provides an application of the SP peptide shown in SEQ ID No.1 or the derivative thereof in preparing medicines for reducing IL-13 level and IL-4 level of a patient with asthma:

Xaa1-Gln-Xaa2-Xaa3-Thr-Ser-Gly-Xaa4 (SEQ ID No.1)

Wherein,
Xaa1 is deletion, Ala, Gly, Val, Leu or Ile,
Xaa2 is Thr or Ser,
Xaa3 is Tyr, Phe or Trp, and
Xaa4 is deletion, Ala, Gly, Val, Leu, Ile or Pro;

The derivative includes a pharmaceutically acceptable salt or ester of the peptide.

Further, the peptide or the derivative thereof is a peptide shown in SEQ ID No.2 or a pharmaceutically acceptable salt or ester thereof:

Gly-Gln-Thr-Tyr-Thr-Ser-Gly (SEQ ID No.2).

Further, the medicine is a unit formulation or an injection formulation.

Further, the unit formulation or the injection formulation contains the peptide or the derivative thereof having an effective therapeutic dosage from 200 to 3000 µg. Furthermore, wherein the unit formulation or the injection formulation contains the peptide or the derivative thereof having an effective therapeutic dosage from 250 to 2500 µg.

For illustrative purposes, the present invention is further described in detail below through specific embodiments. It should be particularly pointed out that, the specific embodiments are not intended to limit the scope of the invention, but only for purposes of explanation. Apparently, in accordance with the description of the present invention, those skilled in the art can make various rectifications and modifications to the present invention, the rectifications and modifications also fall within the scope of the present invention. In addition, the present invention cites open publications for clearly illustrating the present invention, and the contents of which are incorporated herein by its entirety and form a part of the description of the present invention.

DETAILED DESCRIPTION

Embodiment 1

Protective Effect of an SP Peptide on Asthma in a Mouse

1. Experimental Materials
1.1 Animals:

Clean grade ICR mice, half male and half female, body weight of 18 g~22 g, purchased from the Experimental Animal Center of Nantong University.

1.2 Medicines, Reagents and Instruments:

The peptide with following sequence GQTYTSG (hereinafter referred to as SP peptide) is synthesized by an Automatic Peptide Synthesizer model 413A (purchased from Perkin Elmer Company) using a solid phase peptide synthetic method. Refer to the description of Embodiment 1 in PCT/CN2006/001176 for detailed synthetic steps. Dissolve the peptide in physiological saline in use.

Medicines as positive control: dexamethasone injection solution, purchased from Guizhou Huasheng Pharmaceutical Co., Ltd., Specification: 5 mg/ml/piece, human daily dosage 10 mg/70 kg~d.

Ovalbumin (Albumin Egg), purchased from Sigma Company.

Mouse IL-13 ELISA Kit, purchased from Shanghai Blue-Gene Biotech Co., Ltd.

BIO-RAD 680 Bio-Rad Microplate Reader.

1.3 Grouping and Medicinal Dosage

ICR mice, half male and half female, are divided randomly into 9 groups with each group having 10 mice, that is:

1) blank control group (administer an equal volume of physiological saline with a model group);

2) model group (administer ovalbumin and aluminium hydroxide solutions prepared with physiological saline);

3) positive medicines group (administer an equal volume of dexamethasone injection solution with the model group, having the dosage of 0.9 μg/kg·d);

4) SP peptide high-dosage preventive administration group, 5) SP peptide medium-dosage preventive administration group, and 6) SP peptide low-dosage preventive administration group (administer ovalbumin and aluminium hydroxide, and the SP peptides with a respective dosage of 250 μg/kg·d, 125 μg/kg·d and 62.5 μg/kg·d prepared into an SP peptide solution of a desired concentration with physiological saline).

7) SP peptide high-dosage treatment administrative group, 8) SP peptide medium-dosage treatment administration group, and 9) SP peptide low-dosage treatment administration group (administer ovalbumin and aluminium hydroxide, and the SP peptides with a respective dosage of 250 μg/kg·d, 125 μg/kg·d and 62.5 μg/kg·d prepared into an SP peptide solution of a desired concentration with physiological saline).

All dosage groups of the SP peptide are administered by subcutaneous injection with a 0.1 ml SP peptide solution per 10 g weight of a mouse, the blank control group uses the same amount of physiological saline (0.1 ml physiological saline per 10 g weight of a mouse), and the positive medicines group is administered by intraperitoneal injection with 0.1 ml positive medicines per 10 g weight of a mouse.

2. Experimental Method
2.1 Experimental Scheme:

Preparation of sensitized liquid: prepare in a proportion of dissolving 10 ug ovalbumin and 2 mg aluminium hydroxide in 0.5 ml physiological saline, and use it right after being prepared.

The mice in each group are administered in the following manner and fed in a normal way every day during the administration period.

On day 1, day 7 and day 14, the mice of all groups (the model group, the preventive administration groups, the treatment administration groups, and the positive medicines group) apart from the blank control group are injected intraperitoneally with 0.5 ml freshly prepared sensitized liquid. The blank control group is injected intraperitoneally with an equal volume of physiological saline.

Since day 21 (i.e., starting from week 4), the mice of all groups apart from the blank control group are placed in a 16 L closed container every fourth days, make the mice inhale 1 wt % ovalbumin physiological saline by ultrasonic nebulization, with an inhalation duration of 25 min/d and a nebulization flow rate of 3 ml/min, for twice a week to induce asthma, and the process continues until week 19. The mice in the blank control group undergo nebulization intraperitoneally with an equal volume of physiological saline.

Particularly, the preventive administration group (the SP peptide high-dosage preventive administration group, SP peptide medium-dosage preventive administration group, and SP peptide low-dosage preventive administration group) are injected subcutaneously with a corresponding dosage of SP peptide at right hindlimb of the mouse, one hour after the first intraperitoneal injection of the sensitized liquid (i.e., from day 1), and are administered every other day for 15 times in total.

On day 1 of week 15, randomly draw five mice from each group—the model group, the preventive administration groups, the treatment administration groups and the positive medicines group, and after a pathological check, the mice in all asthma groups apart from the preventive administration groups are successfully modeled. From the same day, the mice in the treatment administration groups (SP high-dosage treatment administration group, SP medium-dosage treatment administration group, and SP low-dosage treatment administration group) are injected subcutaneously with a corresponding dosage of SP peptide at right hindlimb thereof, and are administered every other day for 15 times in total. From the same day, the mice in the positive medicines group are injected intraperitoneally with 0.1 ml dexamethasone injection per 10 g weight of a mouse, and are administered every other day for 15 times in total.

As for the determination of the experimental result, all mice are killed to obtain blood by picking off their eyeballs 6 hours after the final nebulization inhalation (week 19), and serum is collected and stored at −70° C. until needed. Double antibody sandwich ELISA method is adopted to detect IL-13 level of the serum with a mouse IL-13 ELISA detection kit, and IL-13 standard is proportionally diluted with diluent in the kit and then is operated according to the specification of the kit. A standard curve is computed, and the values of the detected sample are read from the standard curve and then multiple a dilution factor to obtain a value of IL-13 level of the serum sample. Similar to the method of IL-13, a value of IL-4 level of the serum sample is obtained through a standard curve of an IL-14 standard.

After serum is collected, the mouse lung is first immersed and flushed with chilled physiological saline, then superior lobe of left lung in the mouse is taken and fixed using 10% neutral formalin, embedded with paraffin, sectioned and stained with HE, further dehydrated using a gradient ethanol, clarified in xylene, sealed by neutral balsam, and undergoes histopathologic examination, including: Examine whether the lung tissues show intrapulmonary bronchia and perivascular interstitial edema, and infiltration with inflammatory cells, whether alveolar cavity is clear or has exudant, and whether hyperemia alveolar walls are thickened, and examine major types of inflammatory cells, etc.

Preparation of lung tissue homogenates: after superior lobe of left lung in a mouse is taken, approximately 0.04 g sample is taken from the rest fresh lung tissues, and placed in a grinder, 400 ul chilled PBS (a concentration of 10%) is added in. The sample is grinded in different groups respectively on the ice one by one, and then the mash is sucked, and centrifuged to collect the supernatant for determination. First, 40 ul sample diluent is added to a well of an enzyme-labeled coated plate for sample to be detected, and then add 10 ul homogenate sample to be determined of the mouse lung tissue (the sample to be determined is diluted by a factor of 1:5). Then, for the same serum sample, the IL-4 and IL-13 in lung tissue homogenates of the mouse is determined according to the specification of the ELISA kit.

Lung tissue lesions (including bronchia and perivascular interstitial edema, alveolar wall congestion or emphysema) are marked respectively as 1, 2, 3 and 4 in ascending order of severity, 0 stands for no obvious lesions, and 0.5 for extreme mild lesions. All scores are accumulated, and a mean score (±SD) of each mouse in each group is calculated, and a higher score indicates a more severe level of lesions. Perform a rank-sum test to pathological score results to compare the two samples, and compare with the model group.

2.2 Data Processing: perform data processing to all data, rank-sum test to pathological score, t-test to the other data, and make statistics to analytic results.

3. Results 3.1 IL-13 level and IL-4 level in serum and lung tissue homogenates of the mice FIG. 1 and FIG. 2 respectively show an influence of an SP peptide on IL-13 level and IL-4 level in serums and lung tissue homogenates of each group of mice, wherein the administration dosage is as described in aforementioned 1.3, and results in FIG. 1 and FIG. 2 are mean values of each group of mice.

Figure 1:
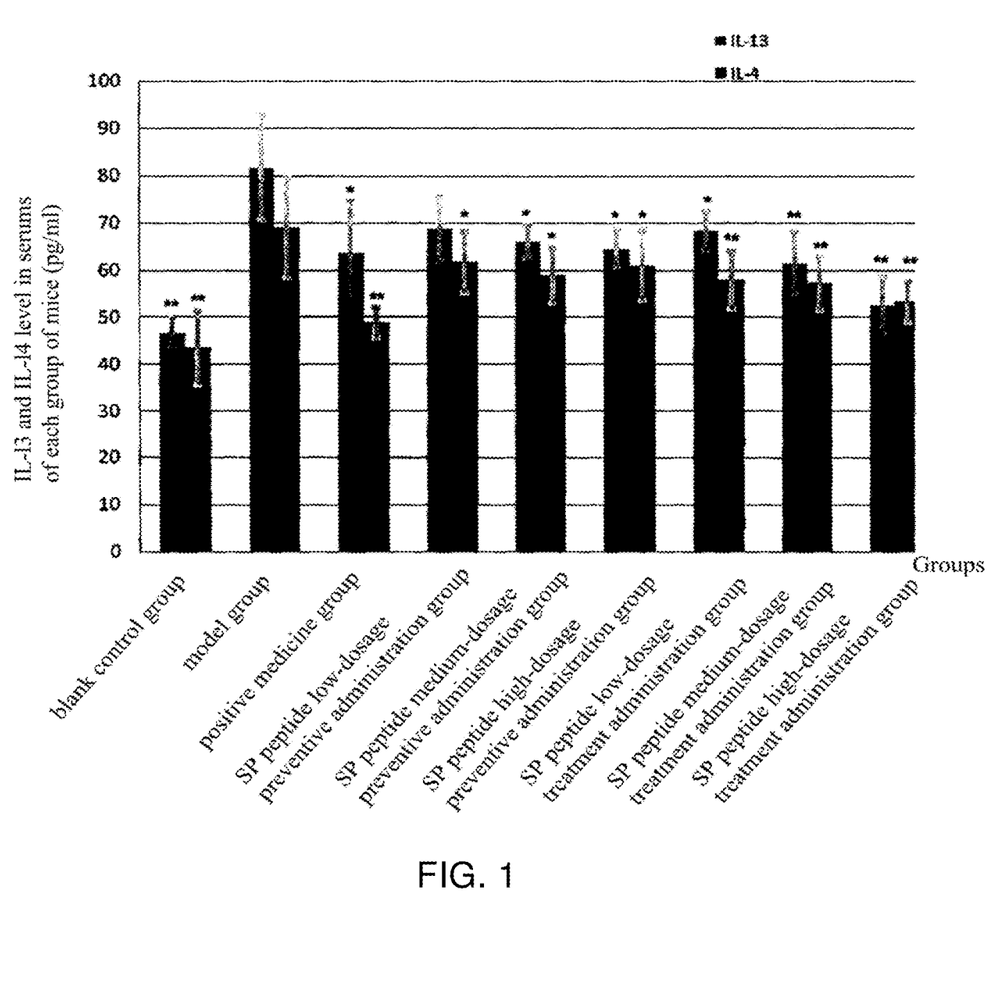
FIG. 1 shows an influence of an SP peptide on IL-13 level and IL-4 level in serums of each group of mice.
Figure 2:
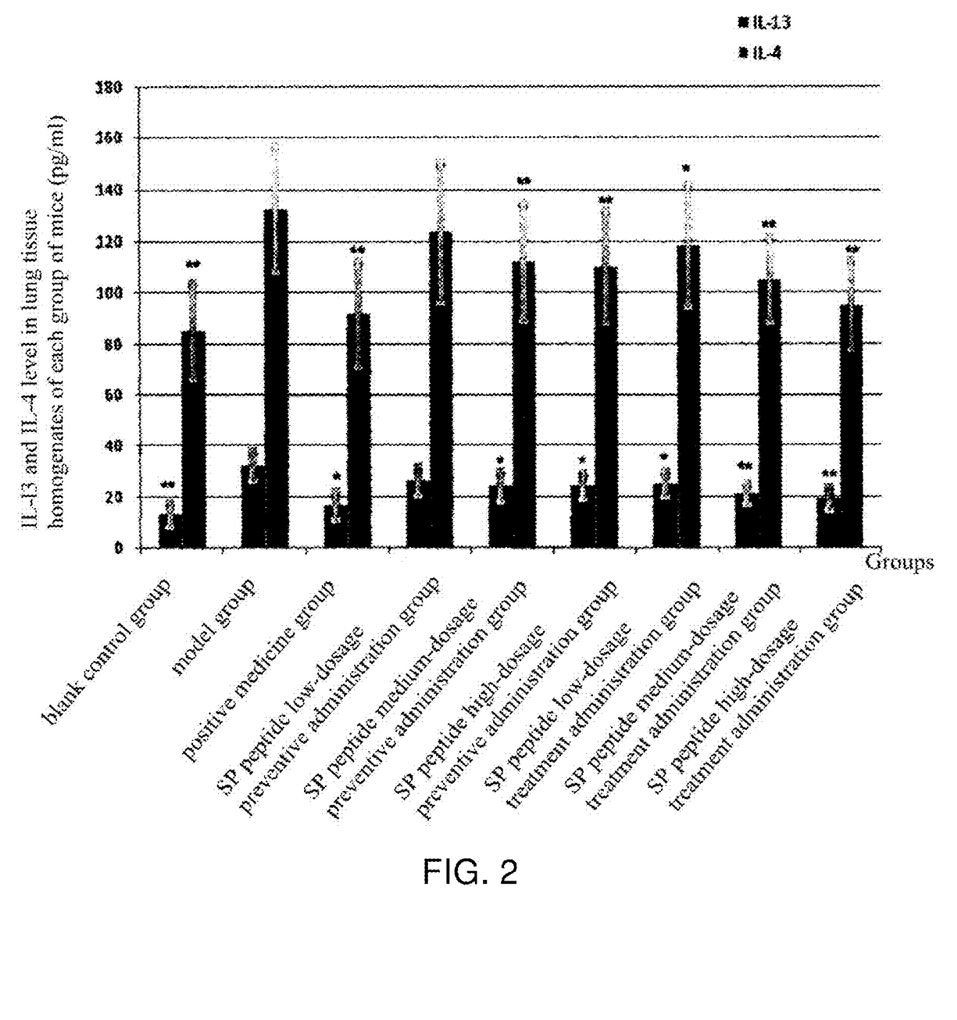
FIG. 2 shows an influence of an SP peptide on IL-13 level and IL-4 level in lung tissue homogenates of each group of mice.

It can be seen from FIG. 1 and FIG. 2 that, the IL-13 level and IL-4 level in serums and lung tissue homogenates of the mouse model with allergic asthma sensitized induced by the combination of ovalbumin and aluminium hydroxide adjuvant are significantly increased ($P<0.01$). It can be known from the following histopathologic test that, the rise in IL-13 level and IL-4 level induces bronchial asthma of mice, which indicates the bronchial asthma of mice sensitized induced by combining ovalbumin and aluminium hydroxide adjuvant can be triggered by releasing IL-13 and IL-14. However, compared to the model group, the IL-13 level and IL-14 level in serums and lung tissue homogenates of the mice in the SP peptide high-/medium-/low-dosage treatment administration group and the SP peptide high-/medium-dosage preventive administration groups are all significantly decreased (* $P<0.05$, ** $P<0.01$).

3.2 Lung Tissue Sections result analysis

Figure 4:
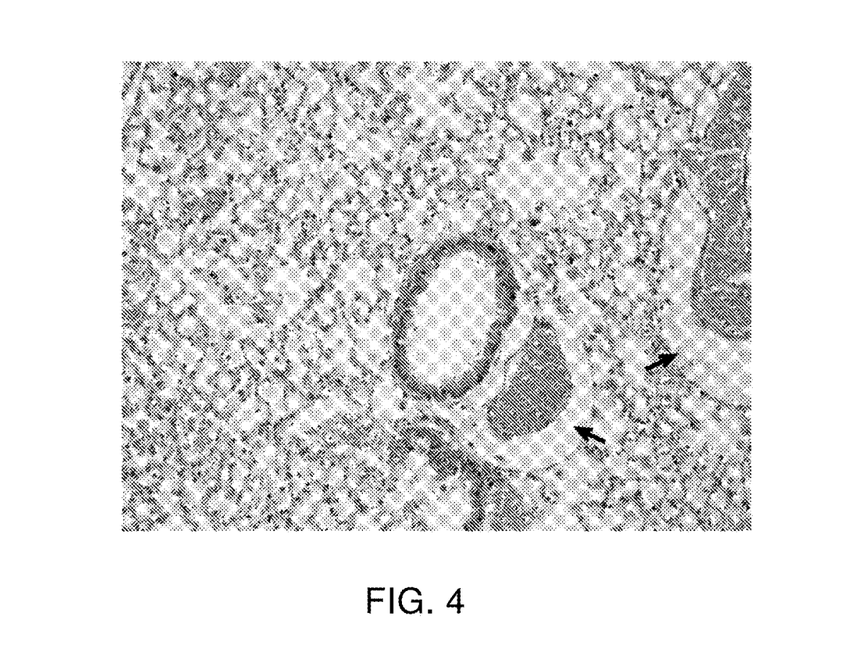
FIG. 4 shows a pathological change of lung tissues of a mouse in a blank control group according to Embodiment 1.

It can be seen from FIG. 4 that, the mice in the blank control group has a wider intrapulmonary small perivascular space, without inflammatory cells infiltration (as shown by arrows in FIG. 4).

Figure 5:
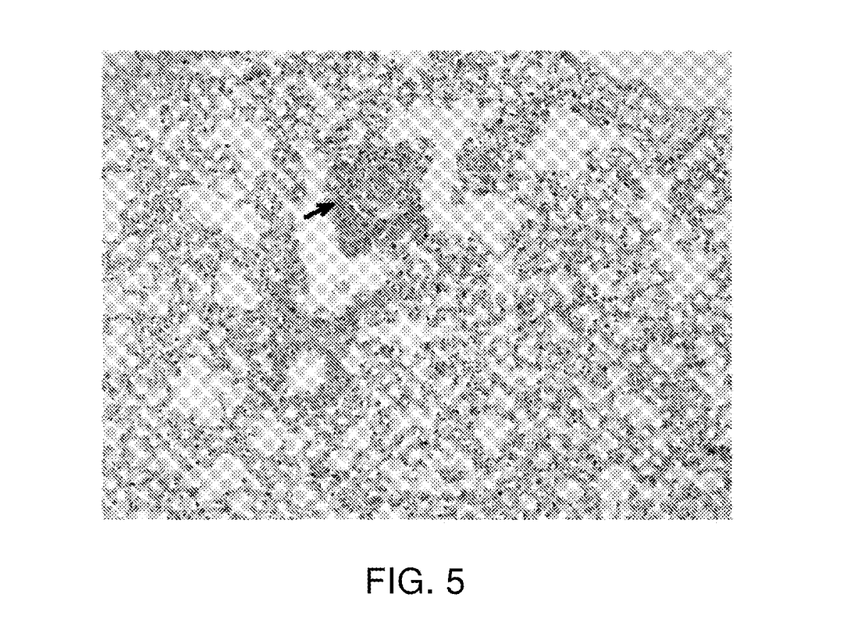
FIG. 5 shows a pathological change of lung tissues of a mouse in a model group according to Embodiment 1.

It can be seen from FIG. 5 that, the mouse in the model group has severe intrapulmonary small perivascular interstitial edema and a massive inflammatory cells infiltration (as shown by arrows in FIG. 5), the inflammatory cells are mainly eosinophils and mononuclear cells, and the alveolar cavity is clear without exudant.

Figure 6:
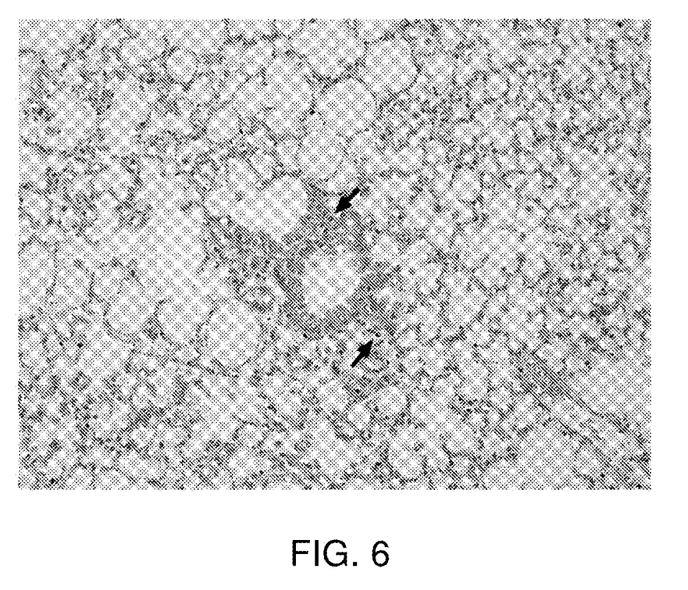
FIG. 6 shows a pathological change of lung tissues of a mouse in a positive medication group according to Embodiment 1.

It can be seen from FIG. 6 that, the mouse in the positive drug group has mild pulmonary interstitial edema and there is infiltration with a few inflammatory cells (as shown by arrows in FIG. 6), the inflammatory cells are mainly eosinophils and mononuclear cells.

Figure 7:
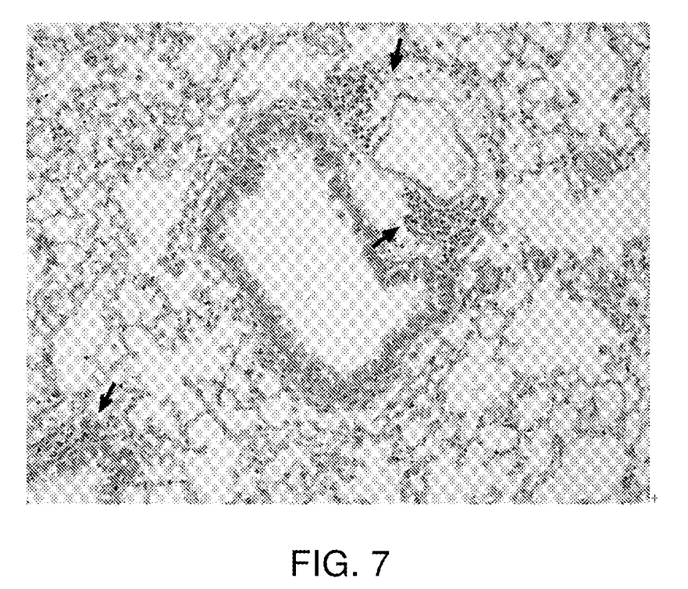
FIG. 7 shows a pathological change of lung tissues of a mouse in an SP peptide low-dosage preventive administration group according to Embodiment 1.

It can be seen from FIG. 7 that, the mouse in the SP peptide low-dosage preventive administration group has a moderate or severe pulmonary interstitial edema and there is infiltration with greater inflammatory cells (as shown by arrows in FIG. 7), the inflammatory cells are mainly eosinophils cells and mononuclear cells.

Figure 8:
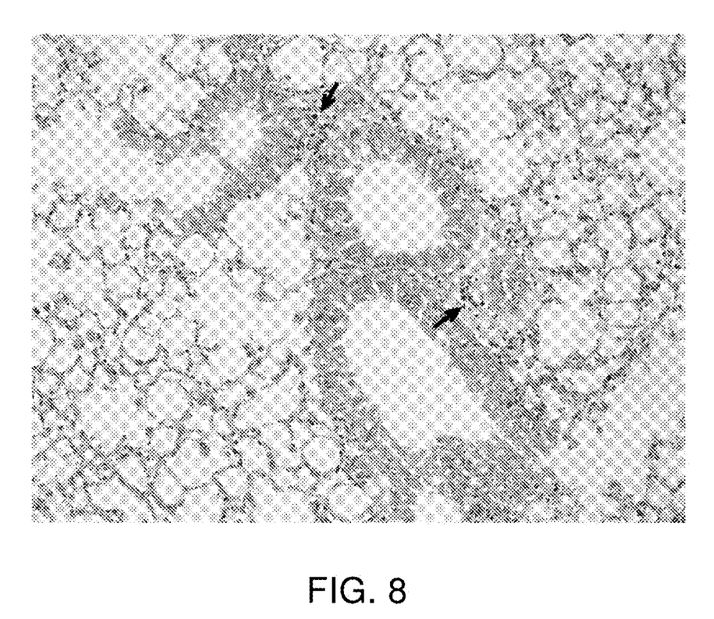
FIG. 8 shows a pathological change of lung tissues of a mouse in an SP peptide medium-dosage preventive administration group according to Embodiment 1.

It can be seen from FIG. 8 that, the mouse in the SP peptide medium-dosage preventive administration group has moderate or mild pulmonary interstitial edema and there is infiltration with a few inflammatory cells (as shown by arrows in FIG. 8), the inflammatory cells are mainly eosinophils and mononuclear cells.

Figure 9:
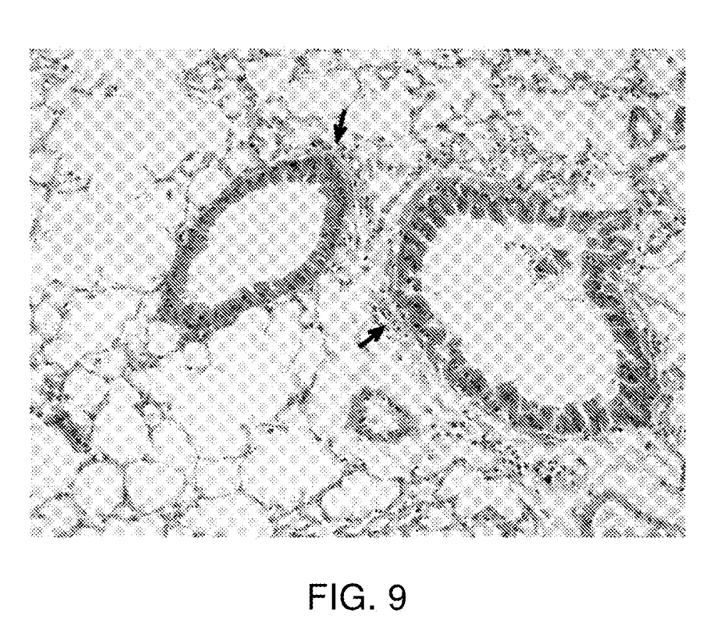
FIG. 9 shows a pathological change of lung tissues of a mouse in an SP peptide high-dosage preventive administration group according to Embodiment 1.

It can be seen from FIG. 9 that, the mouse in the SP peptide high-dosage preventive administration group has mild pulmonary interstitial edema and there is infiltration with a few inflammatory cells around bronchus (as shown by arrows in FIG. 9).

Figure 10:
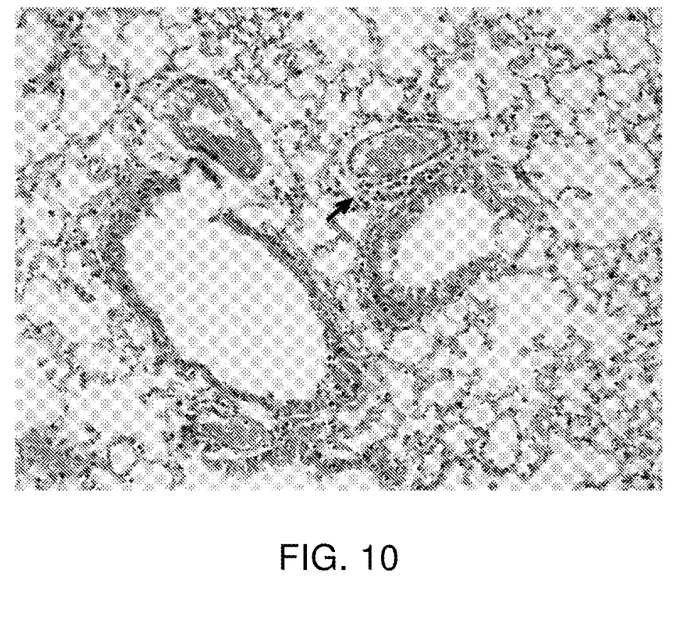
FIG. 10 shows a pathological change of lung tissues of a mouse in an SP peptide low-dosage treatment administration group according to Embodiment 1.

It can be seen from FIG. 10 that, the mouse in the SP peptide low-dosage treatment administration group has moderate intrapulmonary small perivascular and peribronchial pulmonary interstitial edema and there is infiltration with greater inflammatory cells (as shown by arrows in FIG. 10), the inflammatory cells are mainly eosinophils and mononuclear cells.

Figure 11:
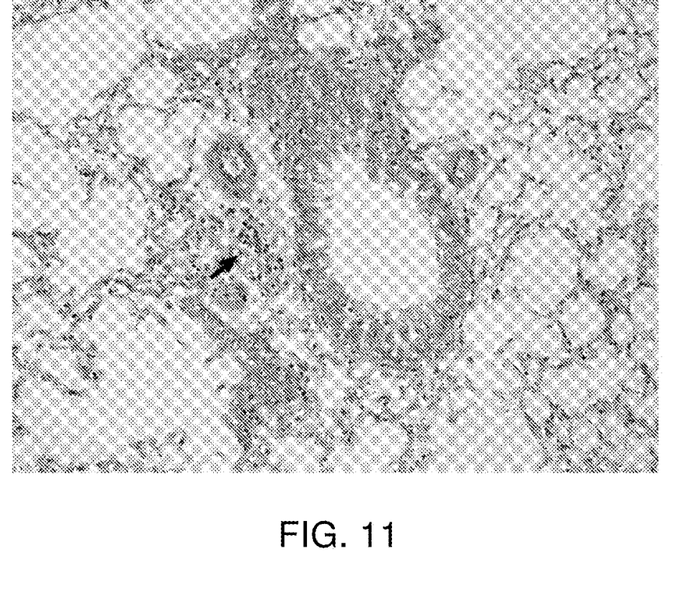
FIG. 11 shows a pathological change of lung tissues of a mouse in an SP peptide medium-dosage treatment administration group according to Embodiment 1.

It can be seen from FIG. 11 that, the mouse in the SP peptide medium-dosage treatment administration group has mild intrapulmonary small perivascular and peribronchial pulmonary interstitial edema and there is infiltration with many inflammatory cells (as shown by arrows in FIG. 11), the inflammatory cells are mainly eosinophils and mononuclear cells, there is congestion around alveolar walls, alveoli are in an emphysematous state.

Figure 12:
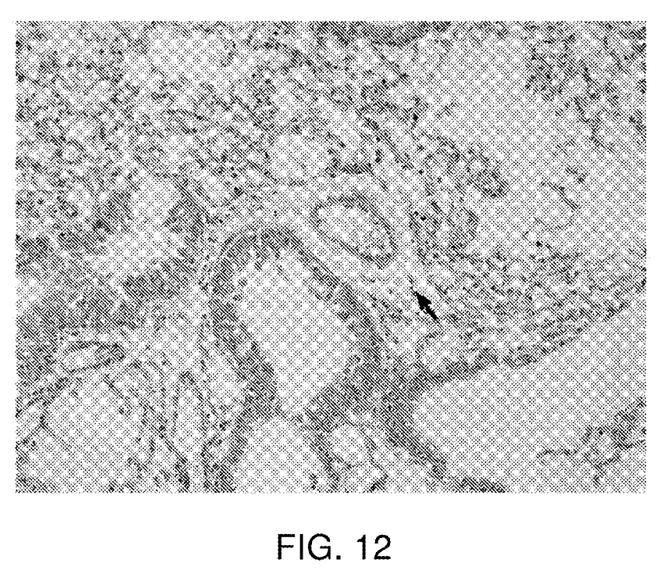
FIG. 12 shows a pathological change of lung tissues of a mouse in an SP peptide high-dosage treatment administration group according to Embodiment 1.

It can be seen from FIG. 12 that, the mouse in the SP peptide high-dosage treatment administration group has mild pulmonary interstitial edema and there is infiltration with a few inflammatory cells (as shown by arrows in FIG. 12), the inflammatory cells are mainly eosinophils and mononuclear cells. (×200)

Figure 3:
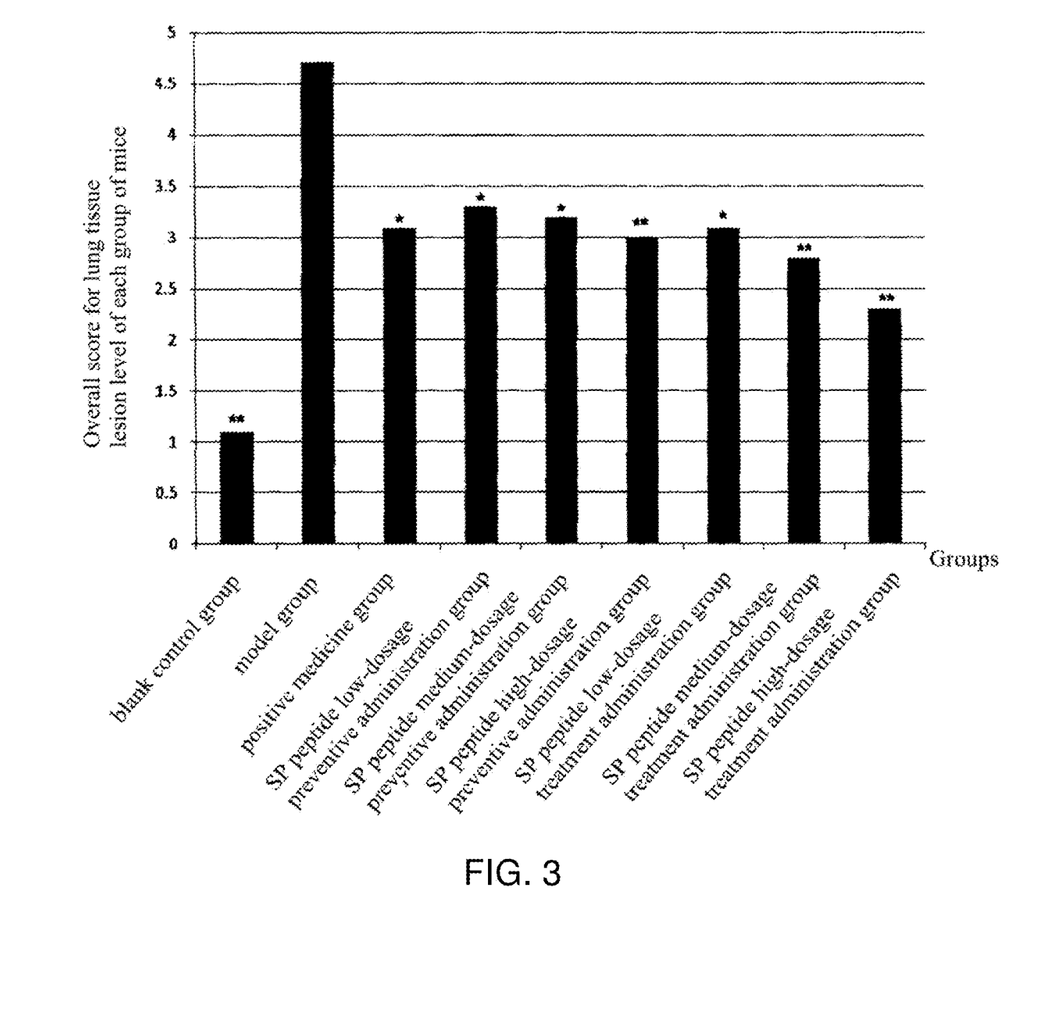
FIG. 3 shows an overall score from lung tissue lesion level of each group of mice.

3.2 As shown in FIG. 3, an overall score result for each pathological test index is obtained by performing a rank-sum test on lung tissue lesion level of each group of mice, according to the above scoring rule. It can be seen from FIG.

3 that, the histopathologic test indicates, bronchia and perivascular interstitial edema, edematous inflammatory cells infiltration, as well as alveolar wall congestion or emphysema are significantly reduced after administering SP peptide for prevention or treatment. In addition, compared to the model group, the mice in the SP peptide low-dosage treatment administration group and the SP peptide medium-/low-dosage preventive administration group all have significant differences (* P<0.05) statistically, wherein compared to the model group, the mice in the SP peptide high-/medium-dosage treatment administration group and the SP peptide high-dosage preventive administration group all have highly significant differences (** P<0.01).

What is claimed is:

1. An application of an SP peptide shown in SEQ ID No.1 or a derivative thereof in treating asthma, comprising: administering a medicine containing the SP peptide or a derivative thereof to a patient in need thereof,
   the derivative comprises a pharmaceutically acceptable salt or ester of the peptide.

2. The application according to claim 1, wherein the peptide or the derivative thereof is a peptide shown in SEQ ID No.2 or a pharmaceutically acceptable salt or ester thereof.

3. The application according to claim 1, wherein the medicine is a unit formulation.

4. The application according to claim 1, wherein the medicine is an injection formulation.

5. The application according to claim 1, wherein the asthma is allergic asthma.

6. A method for treating asthma, comprising: administering a medicine containing therapeutically effective dosage of SP peptide shown in SEQ ID No.1 or a derivative thereof to a patient in need thereof,
   the derivative comprises a pharmaceutically acceptable salt or ester of the peptide.

7. The method according to claim 6, wherein the peptide or the derivative thereof is an SP peptide shown in the following SEQ ID No.2 or a pharmaceutically acceptable salt or ester thereof.

8. The method according to claim 6, comprising: administering the medicine to a patient after asthma attacks so as to treat asthma, the medicine contains 200 to 3000 µg therapeutically effective dosage of the peptide or a derivative thereof.

9. The method according to claim 8, wherein the medicine contains 250 to 2500 µg therapeutically effective dosage of the peptide or a derivative thereof.

10. The method according to claim 6, wherein administering the medicine to the patient with a dosage of unit formulation.

11. The method according to claim 10, wherein the unit formulation contains 200 to 3000 μg therapeutically effective dosage of the peptide or the derivative thereof.

12. The method according to claim 11, wherein the unit formulation contains 250 to 2500 μg therapeutically effective dosage of the peptide or the derivative thereof.

13. The method according to claim 6, comprising: administering the medicine by injection.

14. The method according to claim 6, wherein the asthma is allergic asthma.

15. An application of an SP peptide shown in SEQ ID No.1 or a derivative thereof in reducing IL-13 level and IL-4 level of a patient with asthma, comprising: administering a medicine containing the SP peptide or a derivative thereof to a patient in need thereof, the derivative comprises a pharmaceutically acceptable salt or ester of the peptide.

16. The application according to claim 15, wherein the peptide or the derivative thereof is a peptide shown in SEQ ID No.2 or a pharmaceutically acceptable salt or ester thereof.

17. The application according to claim 15, wherein the medicine is a unit formulation.

18. The application according to claim 15, wherein the medicine is an injection formulation.

19. The application according to claim 15, wherein the asthma is allergic asthma.

* * * * *

SEQUENCE LISTING

```
<160> NUMBER OF SEQ ID NOS: 2

<210> SEQ ID NO 1
<211> LENGTH: 8
<212> TYPE: PRT
<213> ORGANISM: Artificial Sequence
<220> FEATURE:
<223> OTHER INFORMATION: SP peptide shown in Formula I
<220> FEATURE:
<221> NAME/KEY: MISC_FEATURE
<222> LOCATION: (1)..(1)
<223> OTHER INFORMATION: Xaa is deletion, Ala, Gly, Val, Leu or Ile.
<220> FEATURE:
<221> NAME/KEY: MISC_FEATURE
<222> LOCATION: (3)..(3)
<223> OTHER INFORMATION: Xaa is Thr or Ser.
<220> FEATURE:
<221> NAME/KEY: misc_feature
<222> LOCATION: (4)..(4)
<223> OTHER INFORMATION: Xaa is Tyr, Phe or Trp.
<220> FEATURE:
<221> NAME/KEY: MISC_FEATURE
<222> LOCATION: (8)..(8)
<223> OTHER INFORMATION: Xaa is deletion, Ala, Gly, Val, Leu, Ile or
      Pro.

<400> SEQUENCE: 1

Xaa Gln Xaa Xaa Thr Ser Gly Xaa
1               5

<210> SEQ ID NO 2
<211> LENGTH: 7
<212> TYPE: PRT
<213> ORGANISM: Artificial Sequence
<220> FEATURE:
<223> OTHER INFORMATION: SP peptide shown in Formula II

<400> SEQUENCE: 2

Gly Gln Thr Tyr Thr Ser Gly
1               5
```